(12) United States Patent
Shah et al.

(10) Patent No.: US 7,169,755 B2
(45) Date of Patent: *Jan. 30, 2007

(54) SOLUTION FOR REMOVING CATARACTS VIA LIQUEFRACTURE

(75) Inventors: Mandar V. Shah, Arlington, TX (US); Glenn Sussman, Lake Forest, CA (US); Donald M Cohen, Irvine, CA (US); Uday Doshi, Randolph, NJ (US); Kerry L. Markwardt, Mansfield, TX (US)

(73) Assignee: Alcon, Inc., Hunenberg (CH)

( * ) Notice: Subject to any disclaimer, the term of this patent is extended or adjusted under 35 U.S.C. 154(b) by 224 days.

This patent is subject to a terminal disclaimer.

(21) Appl. No.: 10/433,166

(22) PCT Filed: Dec. 11, 2001

(86) PCT No.: PCT/US01/47635

§ 371 (c)(1),
(2), (4) Date: May 30, 2003

(87) PCT Pub. No.: WO02/49552

PCT Pub. Date: Jun. 27, 2002

(65) Prior Publication Data

US 2004/0053818 A1    Mar. 18, 2004

Related U.S. Application Data

(60) Provisional application No. 60/257,715, filed on Dec. 20, 2000.

(51) Int. Cl.
*A61K 38/16* (2006.01)
*A61M 37/00* (2006.01)

(52) U.S. Cl. .......................... 514/8; 606/107; 604/141; 604/403

(58) Field of Classification Search ............... 514/8
See application file for complete search history.

(56) References Cited

U.S. PATENT DOCUMENTS

| | | | |
|---|---|---|---|
| 4,238,482 A | 12/1980 | Peyman et al. | |
| 4,255,415 A | 3/1981 | Chrai et al. | |
| 4,271,143 A | 6/1981 | Schoenwald et al. | |
| 4,861,760 A | 8/1989 | Mazuel et al. | |
| 4,983,585 A | 1/1991 | Pennell et al. | |
| 5,068,225 A | 11/1991 | Pennell et al. | |
| 5,156,839 A | 10/1992 | Pennell et al. | |
| 5,273,056 A * | 12/1993 | McLaughlin et al. | 128/898 |
| 5,409,904 A | 4/1995 | Hecht et al. | |
| 5,422,376 A * | 6/1995 | Webb | 514/781 |
| 5,578,578 A | 11/1996 | Hecht et al. | |
| 5,616,120 A | 4/1997 | Andrew et al. | |
| 5,885,243 A | 3/1999 | Capetan et al. | |
| 5,989,212 A | 11/1999 | Sussman et al. | |
| 5,997,499 A | 12/1999 | Sussman et al. | |
| 6,080,128 A | 6/2000 | Sussman et al. | |
| 6,179,805 B1 * | 1/2001 | Sussman et al. | 604/27 |
| 6,261,547 B1 | 7/2001 | Bawa et al. | |
| 6,403,609 B1 | 6/2002 | Asgharian | |

FOREIGN PATENT DOCUMENTS

| | | |
|---|---|---|
| EP | 0962204 | 12/1999 |
| GB | 2204238 | 11/1988 |
| WO | WO 94/10976 | 5/1994 |
| WO | WO 99/06023 | 2/1999 |
| WO | WO 99/51273 | 10/1999 |

OTHER PUBLICATIONS

Assia, et al. "Experimental Studies on Viscofluids for Intraocular Surgery", *Journal of Cataract and Refractive Surgery*, vol. 24, Jan. 1998, pp. 78-83.
Beesley, et al. "The Effects of Prolonged Phacoemulsification Time on the Corneal Endothelium", *Ann Ophthalmol*, vol. 18, 1986, pp. 216-222.
METHOCEL Cellulose Ethers Technical Handbook, *Dow Chemical Company*, 1997, pp. 1-29.
Fernandez-Vigo, et al., "Elimination of Hydroxypropyl Methylcellulose from the Anterior Chamber of the Rabbit", *Journal of Cataract and Refractive Surgery*, vol. 15, Mar. 1989, pp. 191-195.
Fernandez-Vigo, et al., "Molecular Weight Dependence of the Pharmacokinetic of Hydroxypropyl Methylcellulose in the Vitreous", *Journal of Ocular Pharmacology*, vol. 6, No. 2, 1990, pp. 137-142.
"Final Report on the Safety Assessment of Hydroxyethylcellulose, Hydroxypropylcellulose, Methylcellulose, Hydroxypropyl Methylcellulose, and Cellulose Gum", *Journal of the American College of Toxicology*, vol. 5, No. 3, 1986, pp. 1-59.
Gorzinski, et al., "The Fate of Ultra-Low Viscosity $^{14}$C-Hydroxypropyl Methylcellulose in Rats Following Gavage Administration", *Drug and Chemical Toxicology*, vol. 9, No. 2, 1986, pp. 83-100.

(Continued)

*Primary Examiner*—Cecilia J. Tsang
*Assistant Examiner*—Maury Audet
(74) *Attorney, Agent, or Firm*—Gregg C. Brown

(57) ABSTRACT

An improved solution for use in the removal of cataractous lenses via liquefracture is described. The liquefracture solution contains a viscosity-enhancing agent to increase the residence time of the solution in the heating chamber of the liquefracture handpiece, thereby increasing the expulsion force of the solution from the handpiece (i.e., "pulse force"). An agent that releases gas when the liquefracture solution is heated in the handpiece may also be included in the solution, thereby also enhancing the pulse force of the solution upon expulsion from the handpiece. The solution preferably also contains a partially water-soluble agent that forms a temporarily insoluble precipitate when heated in a liquefracture handpiece. The precipitate acts as an abrasive agent when expelled with the liquefracture solution from the handpiece, thereby facilitating the cutting and disintegration of the cataractous lens material.

13 Claims, No Drawings

OTHER PUBLICATIONS

BSS Plus Overview, *BSS Plus Sterile Intraocular Irrigating Solution*, Alcon intranet information.

BSS Plus Serile Irrigating Solution (balanced salt solution), *Physicians' Desk Reference for Ophthalmology*, 26th Edition, 1998, p. 209.

Cellugel® Ophthalmic Viscosurgical Device Package Insert, 4 pages.

Celoftal™ Ophthalmic Viscosurgical Device (2% Hydroxypropyl Methycellulose) Package Insert, 2 pages.

Ocucoat® Viscoadherent (2% Hydroxypropylmethylcellulose) Package Insert, 6 pages.

* cited by examiner

SOLUTION FOR REMOVING CATARACTS VIA LIQUEFRACTURE

This application claims priority from International Patent Application No. PCT/US01/47635 filed on Dec. 11, 2001, which claims priority from U.S. Provisional Application Ser. No. 60/257,715, filed on Dec. 20, 2000.

BACKGROUND OF THE INVENTION

The present invention is directed to the field of ophthalmic surgery. More specifically, the invention is directed to the field of procedures and associated products for removing the natural crystalline lens of the human eye in patients whose lenses have become afflicted with cataracts or other conditions wherein removal of the lenses is required.

Removal of human lenses has been achieved by various surgical techniques in the past. The most prevalent technique at this time involves a process known as "phacoemulsification". This process involves the use of a handpiece with a tip that vibrates at an ultrasonic frequency. After making a small incision in the eye, the ophthalmic surgeon employs this handpiece to emulsify the lens within the capsular bag of the eye, and then employs the irrigation and aspiration modes of the handpiece to remove the lens particles from the capsular bag. Millions of cataract patients have had their cataractous lenses removed by means of the phacoemulsification procedure. Although ophthalmic surgeons have mastered the use of the phacoemulsification handpiece and associated surgical techniques, the use of an ultrasonic needle or tip within the eye presents inherent risks and concerns. Ophthalmic surgeons and others skilled in the art have therefore searched for improved devices and procedures for removing the human lens.

A new lens removal procedure known as "liquefracture" is currently being developed by Alcon Research, Ltd. This procedure is described in U.S. Pat. No. 5,616,120 (Andrew, et al.), U.S. Pat. No. 5,885,243 (Capetan, et al.), U.S. Pat. No. 5,989,212 (Sussman, et al.), U.S. Pat. No. 5,997,499 (Sussman, et al.) and U.S. Pat. No. 6,080,128 (Sussman, et al.), the entire contents of the foregoing patents are hereby incorporated in the present specification by reference.

Liquefracture is a new technique wherein the lens is disintegrated by applying hot pulses of a solution to the lens via an irrigation/aspiration handpiece. The handpiece, such as those described in the above-cited patents, includes a chamber for heating the solution and generating pulses of heated solution that are expelled from the handpiece. The lens is disintegrated by means of a combination of the heat absorbed from the solution and the force of the pulses of the solution impacting the lens tissue. The solution utilized for this purpose is referred to herein as the "liquefracture solution".

Due to the delicacy of the intraocular tissues, both the extent to which the solution can be heated and the force or velocity of the pulses are necessarily constrained. In order to prevent damage to surrounding tissues, the stream of hot, pulsed solution is surrounded by a conventional irrigating solution which dissipates both the heat and force of the pulsed solution after it impacts the lens tissue. This second solution is referred to herein as either the "irrigating solution" or the "outer" or "dissipating" solution.

Prior to the present invention, the solution utilized for both the liquefracture solution and the irrigating solution has been a conventional balanced salt solution such as BSS® (Balanced Salt Solution) Sterile Irrigating Solution, which is available from Alcon Laboratories, Inc., Fort Worth, Tex. Although this type of solution is generally adequate, there is a need for improved solutions which enhance the disintegration of the lens with the pulsed, heated solution and facilitate removal of the lens fragments following disintegration of the lens. The present invention is directed to filling this need.

SUMMARY OF THE INVENTION

The present invention is based on the discovery of a means for enhancing the effectiveness of the liquefracture solution in disintegrating the lens material during the above-described liquefracture procedure. More specifically, it has been discovered that the effectiveness of the liquefracture solution can be enhanced by increasing the pulse force of the solution. The effectiveness of the liquefracture solution can be further enhanced by including an agent which forms a temporarily insoluble precipitate at the temperatures utilized to form the hot, pulsed solution, thereby resulting in particles that act as abrasive agents.

The pulse force of the liquefracture solution is increased by including a viscosity-enhancing agent in the solution used to form the hot, pulsed solution, thereby increasing the length of time for which the solution is retained in the heating/expansion chamber of the liquefracture handpiece and permitting more energy to be stored in the pulse of fluid. The pulse force can be further enhanced by including a small amount of a gas-generating propellant in the solution used to form the hot, pulsed solution, thereby increasing the velocity or force of the hot pulsed solution.

In a preferred embodiment of the present invention, the effectiveness of the liquefracture procedure is further enhanced by including a viscosity-enhancing agent in the irrigating solution utilized as the outer or dissipating solution in the procedure. The enhanced viscosity of the irrigating solution increases the ability of the solution to dissipate the heat absorbed from the liquefracture solution. As a result, the temperature or proportion of the liquefracture solution can be increased (i.e., relative to the irrigating solution), thereby further enhancing the ability of the liquefracture solution to disintegrate the lens material.

The increased pulse force of the solutions of the present invention enhances the effectiveness of the liquefracture procedure, relative to the speed at which the lens is disintegrated and the extent to which liquefracture can be utilized to remove relatively hard lenses. The inclusion of an abrasive agent in the solutions further enhances the effectiveness of the liquefracture solution by increasing the ability of the solutions to cut and disintegrate cataractous lens material.

DETAILED DESCRIPTION OF THE INVENTION

The improved liquefracture solutions of the present invention have been discovered as a result of a careful balancing of several factors. For example, the desired goal of enhancing the ability of the liquefracture solution to disintegrate the lens must be balanced against other required physical characteristics of the solution, such as the need for the solution to flow through the liquefracture handpiece and associated surgical equipment during the surgical procedure.

The ability of a liquefracture solution to disintegrate a cataractous lens is directly dependent on the force of the pulsed solution as it impacts the lens tissue. This force is referred to herein as the "pulse force" of the liquefracture solution. As indicated above, it has been discovered that the pulse force of the liquefracture solution can be increased by enhancing the viscosity of the liquefracture solution. Enhancing the viscosity of the liquefracture solution increases the residence time of the solution in the heating chamber of the liquefracture handpiece, thereby increasing the energy absorbed by the solution and increasing the force by which the solution is expulsed from the chamber.

Various types of agents may be utilized to enhance the viscosity of the liquefracture solution, such as chondroitin sulfate, sodium hyaluronate or other proteoglycans; cellulose derivatives, such as hydroxypropyl methylcellulose ("HPMC"), carboxy methylcellulose ("CMC"), and hydroxyethyl cellulose ("HEC"); collagen and modified collagens; galactomannans, such as guar gum, locust bean gum and tara gum, as well as polysaccharides derived from the foregoing natural gums and similar natural or synthetic gums containing mannose and/or galactose moieties as the main structural components (e.g., hydroxypropyl guar); xanthan gum; gellan gums; alginate; chitosans; polyvinyl alcohol; carboxyvinyl polymers (e.g., carbomers such as the Carbopol™ brand polymers available from B.F. Goodrich); and various other viscous or viscoelastomeric substances, including but not limited to those described in U.S. Pat. No. 5,409,904 (Hecht, et al.), the entire contents of which are hereby incorporated by reference in the present specification.

The following patent publications may be referred to for further details concerning the above-listed viscosity-enhancing agents: U.S. Pat. No. 4,861,760 (gellan gums); U.S. Pat. No. 4,255,415 and WIPO Publication No. WO 94/10976 (polyvinyl alcohol); U.S. Pat. No. 4,271,143 (carboxyvinyl polymers); WIPO Publication No. WO 99/51273 (xanthan gum); and WIPO Publication No. WO 99/06023 (galactomannans). The entire contents of the foregoing references pertaining to the structures, chemical properties and physical properties of the respective viscosity enhancing agents described above are hereby incorporated in the present specification by reference.

As demonstrated in Example 8 below, it has been found that the use of higher molecular weight fractions of polymeric materials as the viscosity enhancing agent is desirable, because the higher molecular weight fractions generally produce greater pulse forces than lower molecular weight fractions of the same material. The use of higher molecular weight fractions is therefore preferred.

The most preferred viscosity-enhancing agent is HPMC at a molecular weight of 86,000 to 260,000. As discussed below, HPMC is also preferred as the transient abrasive agent of the improved liquefracture solutions described herein.

The above-described viscosity-adjusting agents will be utilized in an amount sufficient to provide the liquefracture solutions of the present invention with an enhanced viscosity. As utilized herein, the phrase "enhanced viscosity" means a viscosity which is greater than the viscosity of aqueous humor and standard irrigating solutions, both of which generally have viscosities of approximately 1 centipoise ("cps"). The liquefracture solutions of the present invention will typically have viscosities of from greater than 1 cps to about 15 cps, preferably from about 2 to about 7 cps.

The liquefracture solutions of the present invention contain one or more of the above-described viscosity enhancing agents in an ophthalmic acceptable vehicle. Various types of solutions may be utilized as a vehicle for the liquefracture solution; however, the conductivity of the liquefracture solution is a factor which must be taken into account relative to selection of an appropriate vehicle.

Due to the very high resistance of water, which results in low conductivity, water does not heat up sufficiently and thus does not produce adequate pulse force for liquefracture procedures. Ionic solutions, such as balanced salt solution, have relatively lower resistance to electricity, and therefore have higher conductivity. This higher conductivity allows the ionic salt solutions to be heated sufficiently to be utilized in liquefracture. However, the conductivity of the solution has to be balanced with instrument design criteria, such as the need to avoid corrosion or other damage to the liquefracture handpiece and avoid clogging of the handpiece or other fluid channels in the ophthalmic surgical operating system.

The liquefracture solutions are preferably formulated to be isotonic. The osmolality of the solution is an indirect measure of conductivity, since both properties are dependent on the ionic concentration. The liquefracture solutions of the present invention preferably have an osmolality of from about 200 to about 400 milliosmoles per kilogram of water (mOsm/kg").

As indicated above, the pulse force of the liquefracture solution of the present invention may also be enhanced by the inclusion of a propellant in the solution. The propellant comprises a gas liberating substance, such as sodium bicarbonate or sodium chlorate. In a preferred embodiment of the present invention, the liquefracture solution contains sodium bicarbonate or sodium chlorate in a concentration of from about 1.0 to about 2.5 w/v %.

The ability of the liquefracture solutions of the present invention to cut and disintegrate cataractous lens tissue can be further improved by including a transient abrasive agent in the solutions. The transient abrasive agent forms a temporarily insoluble precipitate when heated in the liquefracture handpiece, thereby creating particles that facilitate cutting and disintegration of the cataractous lens when pulses of the hot liquefracture solution are applied to the lens, but returns to solution as the liquefracture solution cools within the eye, thereby facilitating removal of the solution via aspiration. This transient, temperature dependent formation of a precipitate within the liquefracture solution significantly enhances the ability of the solution to cut and disintegrate the cataractous lens, without disrupting the operation of the irrigation and aspiration modes of ophthalmic surgical systems. The materials that perform these functions are referred to herein as "transient abrasive agents".

Various physiologically acceptable materials may be utilized as the transient abrasive agent. In addition to being physiologically acceptable, generally, and non-toxic to intraocular tissues, specifically, the transient abrasive agent must be: (1) at least partially soluble in aqueous electrolyte solutions at room temperature and body temperature (i.e., temperatures of about 25° C. and 37° C., respectively), (2) substantially insoluble at a temperature greater than 50° C. and (3) chemically stable at the aforementioned temperatures. Materials that meet these criteria are referred to herein as being "an ophthalmically acceptable, transient abrasive agent".

The preferred transient abrasive agents are cellulose derivatives, such as hydroxypropyl methylcellulose ("HPMC"), carboxy methylcellulose ("CMC") and hydroxyethyl cellulose ("HEC"). The most preferred cellulose derivative is HPMC. HPMC is preferred based on its unique ability to form a temporarily insoluble precipitate upon heating to temperatures above 50° C. The other cellulose derivatives mentioned above will also form an insoluble precipitate when heated, but only a relatively small portion of these cellulose materials becomes insoluble.

The selection of an ideal concentration for each class or type of transient abrasive agent requires a balancing of the above-cited factors. However, the concentrations selected will generally be in the range of from about 0.05 to about 0.5 weight/volume percent (w/v %).

In a preferred embodiment of the present invention, hydroxypropyl methylcellulose ("HPMC") is utilized as the transient abrasive agent, and also increases the viscosity of the liquefracture solution, thereby enhancing both the pulse force and cutting action of the liquefracture solution.

As indicated above, it is necessary to achieve a balance between enhancing the pulse force of the liquefracture solution, and maintaining a solution viscosity which is acceptable for use with the irrigating/aspiration systems employed in intraocular surgical procedures. If HPMC is used to enhance the viscosity of the liquefracture solution and also as the transient abrasive agent, then there is an additional constraint, that is, the concentration of HPMC should not be such that its particles would clog the heating chamber of the liquefracture handpiece. The use of HPMC concentrations of 0.2% or higher may result in a clogging of the irrigation/aspiration system. Consequently, it is preferred to utilize HPMC concentrations of less than 0.2 w/v %.

It should be noted that there is wide molecular weight range for HPMC. Increasing the molecular weight of HPMC will provide a higher viscosity at the same concentration level. In order to achieve the same viscosity, a lower concentration of higher molecular weight HPMC can be used, resulting in a lower number of particles, and hence, less potential for clogging. These two aspects of HPMC must be balanced to achieve an optimum solution. However, the use of relatively high molecular weight forms of HPMC is preferred for the reasons stated above.

In a preferred embodiment of the present invention, the overall performance of the liquefracture procedure is further enhanced by utilizing an irrigating solution having an enhanced viscosity as the outer or dissipating solution. The use of an enhanced viscosity solution increases the ability of the solution to dissipate heat from the hot, pulsed liquefracture solution, thereby making it possible to increase the temperature of the liquefracture solution and/or increase the proportion of that solution, relative to the irrigating solution. The viscosity-enhancing agents that may be employed for this purpose are the same as those that may be employed to enhance the viscosity of the liquefracture solution. One or more viscosity-enhancing agents is preferably utilized in an amount sufficient to provide the irrigating solution with a viscosity in the range of from about 2 to about 7 cps.

The following examples are provided to further illustrate the liquefracture solutions of the present invention.

EXAMPLE 1

| Component | Amount (w/v %) | Function |
| --- | --- | --- |
| HPMC (E4M) | 0.05 to 0.2 | VEA/TAA* |
| Sodium Bicarbonate | 1.5 | Propellant |
| Hydrochloric Acid | Adjust pH | pH Adjust |
| Sodium Hydroxide | Adjust pH | pH Adjust |
| Water for Injection | 100% | Vehicle |

*VEA/TAA = Viscosity Enhancing Agent/Transient Abrasive Agent

The above-described formulation may be prepared as follows: First, the water for Injection is brought close to boiling or at boiling. The HPMC is then slowly added to the water under continuous stirring to thoroughly disperse it in the water. Then the mixture is slowly allowed to cool, stirring continuously. Once at room temperature, the mixture should start clearing up. Then the mixture is stored overnight in an appropriate container to fully hydrate the HPMC. The following day, the remaining ingredients are added to the HPMC solution, additional water for injection is added if needed to bring the solution to final volume, and the final solution is filtered, packaged in bottles and autoclaved.

EXAMPLE 2

| Component | Amount (w/v %) | Function |
| --- | --- | --- |
| HPMC (K100M) | 0.05 to 0.2 | VEA/TAA |
| Sodium Bicarbonate | 1.5 | Propellant |
| Hydrochloric Acid | Adjust pH | PH Adjust |
| Sodium Hydroxide | Adjust pH | PH Adjust |
| Water for Injection | 100% | Vehicle |

The above-described formulation may be prepared utilizing the method described in Example 1, above.

EXAMPLE 3

| Component | Amount (w/v %) | Function |
| --- | --- | --- |
| HPMC (E4M) | 0.05 to 0.2 | VEA/TAA |
| Sodium Chloride | 0.9 | Tonicity Agent |
| Water for Injection | 100% | Vehicle |

The above-described formulation may be prepared utilizing the method described in Example 1, above.

EXAMPLE 4

| Component | Amount (w/v %) | Function |
| --- | --- | --- |
| HPMC (K100M) | 0.05 to 0.2 | VEA/TAA |
| Sodium Chloride | 0.9 | Tonicity Agent |
| Water for Injection | 100% | Vehicle |

The above-described formulation may be prepared utilizing the method described in Example 1, above.

EXAMPLE 5

| Component | Amount (w/v %) | Function |
| --- | --- | --- |
| HPMC (K100M) | 0.01 to 0.2 | VEA/TAA |
| Sodium Chloride | 0.64 | Tonicity Agent |
| Potassium Chloride | 0.075 | Tonicity Agent |
| Calcium Chloride (Dihydrate) | 0.048 | Buffering Agent |
| Magnesium Chloride (Hexahydrate) | 0.03 | Buffering Agent |
| Sodium Acetate (Trihydrate) | 0.39 | Buffering Agent |

-continued

| Component | Amount (w/v %) | Function |
|---|---|---|
| Sodium Citrate (Dihydrate) | 0.17 | Buffering Agent |
| Hydrochloric Acid | Adjust pH | pH Adjust |
| Sodium Hydroxide | To 7.0–7.2 | pH Adjust |
| Water for Injection | Qsd to 100 | Vehicle |

The above-described formulation may be prepared utilizing the method described in Example 1, above.

EXAMPLE 6

| Component | Amount (w/v %) | Function |
|---|---|---|
| Hydroxypropyl Methylcellulose (HPMC) | 0.01 to 0.2 | VEA/TAA |
| Sodium Chloride | 0.744 | Tonicity Agent |
| Potassium Chloride | 0.0395 | Excipient |
| Dibasic Sodium Phosphate (Anhydrous) | 0.0433 | Buffering Agent |
| Sodium Bicarbonate | 0.219% + 20% xs | Excipient |
| Hydrochloric Acid | Adjust pH | pH Adjust |
| Sodium Hydroxide | To 7.0–7.2 | pH Adjust |
| Water for Injection | 100% | Vehicle |

The above-described formulation may be prepared utilizing the method described in Example 1, above.

EXAMPLE 7

The data set forth in the following table demonstrates the increased pulse force that is achieved by the present invention. More specifically, the data show that the addition of a gas-generating propellant (i.e., sodium bicarbonate) enhances the pulse force of a liquefracture solution upon expulsion from the liquefracture handpiece, and show that the addition of a viscosity-enhancing agent (i.e., HPMC) to the liquefracture solution further increases pulse force.

TABLE 1

| Formulation Description | Pulse Force (g) | Passive Flow (gms/min) |
|---|---|---|
| Distilled Water | 0 | 3.44 |
| BSS ® | 5–5.5 | 3.44 |
| BSS PLUS ® (Part I) | 5.5 | 3.36 |
| 1% NaHCO$_3$ | 6.0 | 3.13 |
| 1% NaHCO$_3$ + 0.1% HPMC (E4M grade) | 6.75 | 3.96 |
| 1.5% NaHCO$_3$ + 0.1% HPMC (E4M grade) | 7.1 | 4.1 |
| 1% NaHCO$_3$ + 0.2% HPMC (E4M Grade) | 8.0 | 4.0 |
| 1.5% NaHCO$_3$ + 0.05% HPMC (K100M grade) | 8.2 | 4.4 |
| BSS PLUS Part I + 0.1% HPMC | 8.5 | 3.96 |

The pulse force evaluations were carried out using an appropriate load cell with an analog-filtered signal, using the following parameters: 10,000 scans/second; 2,000 Hz sampling frequency with 25 Hz high pass cutoff frequency; 2500 Hz low pass cutoff frequency and 2,000 points collected. The full-scale pulse force is measured from the baseline to the maximum height of the filtered signal, which is a relative measurement and not an absolute one.

The electrode or engine was a standard one of the type described U.S. Pat. Nos. 5,989,212; 5,997,499; and 6,080,128 (Sussman et al.), the contents of which have been incorporated herein by reference. The graphite electrodes were set at a pulse duration of 1.7 milliseconds. During the measurement, passive pressure was adjusted such that the passive flow rate was in the range of 3 to 4 grams per minute ("gms/min") for optimal performance of the instrument.

EXAMPLE 8

The effect of the molecular weight of the viscosity enhancing agents on the pulse force of the liquefracture solutions was evaluated by measuring and comparing the pulse forces of solutions containing three different cellulose derivatives, CMC, HPMC and HEC. Solutions containing two different molecular weights of each cellulose derivative were prepared using standard formulation procedures. The concentration of the cellulose polymers was adjusted in order to eliminate differences in viscosity between the test solutions. A standard ophthalmic irrigating solution, BSS™ (Balanced Salt Solution) Sterile Irrigation Solution, was utilized as the control against which the enhanced viscosity solutions were measured. The pulse force of the solutions was determined by means of the procedures described in Example 7. The pulse force values for the test solutions were compared to the pulse force value for the control solution. All of the test solutions demonstrated an increase in pulse force, relative to the control solution. The results, expressed as percent increase in pulse force, are presented in Table 2 below:

TABLE 2

Effect of Molecular Weight on Pulse Force

| Solution | Viscosity (cps) | Mol. Wt. | Increase in Pulse Force (%) |
|---|---|---|---|
| BSS ® Solution | 1.0 | — | — |
| 0.63% NaCMC (7LFPH) | 3.0 ± 0.1 | 90,000 | 35 |
| 0.18% NaCMC (7HFPH) | 3.0 ± 0.1 | 700,000 | 67 |
| 0.2% HPMC (E4M) | 2.9 ± 0.1 | 86,000 | 45 |
| 0.09% HPMC (K100M) | 3.0 ± 0.1 | 260,000 | 105 |
| 0.125% HEC (250M) | 3.0 ± 0.1 | 720,000 | 75 |
| 0.075% HEC (250 HX) | 3.0 ± 0.1 | 1,300,000 | 82 |

The results set forth in Table 2 demonstrate that for a given cellulose derivative, the use of a higher molecular weight fraction of that derivative results in a greater pulse force. This relationship between molecular weight and pulse force may be attributable to the fact that the higher molecular weight polymer material makes the liquefracture solution more cohesive, thereby resulting in a more concentrated force when the heated solution is expelled from the liquefracture handpiece.

The results in Table 2 show that the solution containing HPMC at a molecular weight of 260,000 exhibited a higher pulse force than the solutions containing CMC and HEC at higher molecular weights (i.e., molecular weights of about 700,000). This is believed to be attributable to the fact that the HPMC is acting as both a viscosity enhancing agent and as a transient abrasive agent, and the fact that HPMC is much more effective than CMC or HEC as a transient abrasive agent, as discussed above.

We claim:

1. An improved solution for removing cataracts by means of liquefracture, comprising:
   a viscosity enhancing agent in an amount sufficient to increase the residence time of the liquefracture solution in a heating chamber of a liquefracture handpiece, when said solution is heated in said chamber;
   an ophthalmically acceptable, conductive vehicle for said viscosity-enhancing agent;
   an effective amount of an ophthalmically acceptable, transient abrasive agent; and
   an amount of a gas-generating agent sufficient to enhance the pulse force of the solution upon expulsion of the solution from a liquefracture handpiece.

2. An improved liquefracture solution according to claim 1, wherein the ophthalmically acceptable vehicle comprises a balanced salt solution.

3. An improved liquefracture solution according to claim 2, wherein the solution has an osmolality of 200 to 400 mOsm/kg.

4. An improved liquefracture solution according to claim 2, wherein the solution has a viscosity of from greater than 1 cps to 15 cps.

5. An improved liquefracture solution according to claim 4, wherein the solution has a viscosity of from 2 to 7 cps.

6. An improved liquefracture solution according to claim 1, wherein the viscosity enhancing agent is selected from the group consisting of proteoglycans, cellulose derivatives, collagen and modified collagens, galactomannans, xanthan gum, gellan gums, alginate, chitosans, polyvinyl alcohol, carboxy vinyl polymers and combinations thereof.

7. An improved liquefracture solution according to claim 6, wherein the viscosity enhancing agent is a cellulose derivative.

8. An improved liquefracture solution according to claim 7, wherein the cellulose derivative is selected from the group consisting of HPMC, CMC, HEC and combinations thereof.

9. An improved liquefracture solution according to claim 8, wherein the cellulose derivative comprises HPMC.

10. An improved liquefracture solution according to claim 9, wherein the HPMC has a molecular weight in the range of 86,000 to 260,000.

11. An improved liquefracture solution according to claim 1, wherein the transient abrasive agent is a cellulose derivative.

12. An improved liquefracture solution according to claim 11, wherein the cellulose derivative comprises HPMC.

13. An improved liquefracture solution according to claim 12, wherein the HPMC has a molecular weight in the range of 86,000 to 260,000.

* * * * *